(12) United States Patent (10) Patent No.: US 8,815,514 B2
Satterfield et al. (45) Date of Patent: Aug. 26, 2014

(54) DETECTION PRIMERS FOR NUCLEIC ACID EXTENSION OR AMPLIFICATION REACTIONS

(75) Inventors: Brent C. Satterfield, Greenwood, SC (US); Rebecca Garcia, Greenwood, SC (US)

(73) Assignee: Co-Diagnostics, Inc., Sandy, UT (US)

(*) Notice: Subject to any disclaimer, the term of this patent is extended or adjusted under 35 U.S.C. 154(b) by 164 days.

(21) Appl. No.: 12/830,243

(22) Filed: Jul. 2, 2010

(65) Prior Publication Data

US 2011/0008787 A1 Jan. 13, 2011

Related U.S. Application Data

(60) Provisional application No. 61/222,905, filed on Jul. 2, 2009.

(51) Int. Cl.
*C12Q 1/68* (2006.01)

(52) U.S. Cl.
CPC .................................. *C12Q 1/6825* (2013.01)
USPC ...................... 435/6.12; 536/24.3; 536/24.33

(58) Field of Classification Search
None
See application file for complete search history.

(56) References Cited

U.S. PATENT DOCUMENTS

| 7,276,489 | B2 * | 10/2007 | Agrawal et al. | 514/44 R |
| 2004/0259116 | A1 * | 12/2004 | Beckman et al. | 435/6 |
| 2006/0177842 | A1 * | 8/2006 | Wangh et al. | 435/6 |

OTHER PUBLICATIONS

Ranasinghe et al. (2005) Chem. Commun. pp. 5487-5502.*
Satterfield et al. (2007) Clinical Chemistry vol. 53:12 pp. 2042-2050.*

* cited by examiner

*Primary Examiner* — Suchira Pande
(74) *Attorney, Agent, or Firm* — Meunier Carlin & Curfman, LLC (57) ABSTRACT

Disclosed are methods and compositions related to real-time PCR and other nucleic acid extension or amplification reactions.

8 Claims, 3 Drawing Sheets

Step 1: Primer extension

Step 2: Reverse primer extension

Step 3: Nucleic acid sequence cleaved, increase in signal

B

Step 1: Primer extension

Step 2: Reverse primer extension

Step 3: Nucleic acid sequence displaced, increase in signal

Figure 3.

|  | Sequence |
|---|---|
| SEQ ID NO:1 | CGCCG |
| SEQ ID NO:2 | CGGCG |
| SEQ ID NO:3 | GACGCCGT |
| SEQ ID NO:4 | ACGGCGTC |
| SEQ ID NO:5 | GAACCCACTGCTTAAGCCTCAATA |
| SEQ ID NO:6 | GGAGGCTGTA GGCATAAATT GGT |
| SEQ ID NO:7 | AGGAGGCTGT AGGCATAAAT TGGT |
| SEQ ID NO:8 | CGCGCTACAC TGATGCAT |
| SEQ ID NO:9 | ACGCGCGCTA CACTGATG |
| SEQ ID NO:10 | CGCATCGCTT CTAACGGTGA |
| SEQ ID NO:11 | GAGGGTAGTT CGGGGGAGAA |
| Detection Primer 1 | FAM – CGCCG – 9 Carbon Linker – Dabcyl – CGGCG – GAACCCACTGCTTAAGCCTCAATA |
| Detection Primer 2 | FAM – CGCCG – 9 Carbon Linker – CGGCG – Dabcyl – GAACCCACTGCTTAAGCCTCAATA |

SEQUENCE LISTING

<160> NUMBER OF SEQ ID NOS: 11

<210> SEQ ID NO 1
<211> LENGTH: 5
<212> TYPE: DNA
<213> ORGANISM: Artificial Sequence
<220> FEATURE:
<223> OTHER INFORMATION: Stem constituent

<400> SEQUENCE: 1 cgccg                                                                      5

<210> SEQ ID NO 2
<211> LENGTH: 5
<212> TYPE: DNA
<213> ORGANISM: Artificial Sequence
<220> FEATURE:
<223> OTHER INFORMATION: Stem constituent

<400> SEQUENCE: 2 cggcg                                                                      5

<210> SEQ ID NO 3
<211> LENGTH: 8
<212> TYPE: DNA
<213> ORGANISM: Artificial Sequence
<220> FEATURE:
<223> OTHER INFORMATION: Stem constituent

<400> SEQUENCE: 3 gacgccgt                                                                   8

<210> SEQ ID NO 4
<211> LENGTH: 8
<212> TYPE: DNA
<213> ORGANISM: Artificial Sequence
<220> FEATURE:
<223> OTHER INFORMATION: Stem constituent

<400> SEQUENCE: 4 acggcgtc                                                                   8

<210> SEQ ID NO 5
<211> LENGTH: 24
<212> TYPE: DNA
<213> ORGANISM: HIV

<400> SEQUENCE: 5
gaacccactg cttaagcctc aata                                                 24

<210> SEQ ID NO 6
<211> LENGTH: 23
<212> TYPE: DNA
<213> ORGANISM: Hepatitis B

<400> SEQUENCE: 6
ggaggctgta ggcataaatt ggt                                                  23

<210> SEQ ID NO 7
<211> LENGTH: 24
<212> TYPE: DNA
<213> ORGANISM: Hepatitis B

<400> SEQUENCE: 7
aggaggctgt aggcataaat tggt                                                 24

```
<210> SEQ ID NO 8
<211> LENGTH: 18
<212> TYPE: DNA
<213> ORGANISM: Apicomplexa ssp.

<400> SEQUENCE: 8
cgcgctacac tgatgcat                                                 18

<210> SEQ ID NO 9
<211> LENGTH: 18
<212> TYPE: DNA
<213> ORGANISM: Apicomplexa ssp.

<400> SEQUENCE: 9
acgcgcgcta cactgatg                                                 18

<210> SEQ ID NO 10
<211> LENGTH: 20
<212> TYPE: DNA
<213> ORGANISM: Plasmodium

<400> SEQUENCE: 10
cgcatcgctt ctaacggtga                                               20

<210> SEQ ID NO 11
<211> LENGTH: 20
<212> TYPE: DNA
<213> ORGANISM: Trypanosomatida

<400> SEQUENCE: 11
gagggtagtt cggggagaa                                                20
```

DETECTION PRIMERS FOR NUCLEIC ACID EXTENSION OR AMPLIFICATION REACTIONS

CROSS-REFERENCE TO RELATED APPLICATIONS

This application claims priority to U.S. Provisional Application No. 61/222,905, entitled DETECTION PRIMERS FOR NUCLEIC ACID EXTENSION OR AMPLIFICATION REACTIONS, which was filed on Jul. 2, 2009, the disclosure of which is hereby incorporated by reference in its entirety.

SEQUENCE LISTING

The present application is being filed along with a Sequence Listing in electronic format. The Sequence Listing is provided as a file entitled CDIAG_006A.TXT, created Jul. 2, 2010, which is 2 Kb in size. The information in the electronic format of the Sequence Listing is incorporated herein by reference in its entirety.

BACKGROUND

1. Field

The present technology is related to methods and compositions for real-time PCR and other nucleic acid detection, extension or amplification reactions.

2. Description of the Related Art

Numerous methods of amplification of a nucleic acid are known to those skilled in the art. In general, the amplification of a nucleic acid sequence includes creating one or more copies of the nucleic acid sequence or of a secondary nucleic acid sequence intended to be indicative of the presence of the first nucleic acid. Examples include, but are not limited to, polymerase chain reaction (PCR), rolling circle amplification (RCA), nucleic acid sequence based amplification (NASBA), transcription-mediated amplification (TMA), ligase chain reaction (LCR), loop-mediated isothermal amplification (LAMP), among others. In some technologies, a nucleic acid sequence indicative of the presence of a non-nucleic acid structure (e.g., a protein) is amplified, as in the proximity ligation assay (PLA) and other amplification methods.

Real-time and endpoint detection methods in these amplification reactions can involve the use of dyes that have a different fluorescent output in the presence of double-stranded deoxyribonucleic acids (DNA), the use of sequence-specific probes or the use of primers with attached detection mechanisms. Examples of primers with attached detection mechanisms include SCORPION™ primers (DxS Ltd., Manchester, UK) and AMPLIFLUOR® primers (Millipore, Billerica, Mass.).

SCORPION™ primers have a stem-loop nucleic acid sequence which binds specifically to itself through a scorpion-like orientation or mechanism. Because the stem-loop sequence is specific to the product formed by the primer extension, the design of scorpion primers requires three unique, conserved sequences. In some highly polymorphic organisms, finding even one conserved sequence is difficult, let alone finding three conserved sequences.

Hence, primers such as the AMPLIFLUOR® primer—which has a similar structure to SCORPION™ primers (i.e., a primer attached to a stem-loop structure) but without the requirement of a third conserved binding site—are in demand. However, the AMPLIFLUOR® detection method works by incorporating the hairpin structure into the amplified product, and therefore requires a conserved sequence sufficiently long to bind both the primer and the sequence from a stem-loop structure. A method that allows for more flexibility in designing detection primers for unique, conserved regions is therefore needed.

SUMMARY

The embodiments described herein generally relate to methods and compositions for real-time PCR and other nucleic acid amplification or extension reactions.

Some embodiments relate to a Nucleic acid-based detection mechanism. This mechanism may include, for example, a first nucleic acid sequence, a second nucleic acid sequence sufficiently complementary to at least a portion of the first nucleic acid sequence to allow formation of a double-stranded DNA molecule under normal DNA hybridization conditions, a non-nucleic acid linker connecting the first and second nucleic acid sequences, and a signaling element. The signaling element may include, for example, a single signaling molecule, a pair of signaling molecules, a signaling molecule and a quenching molecule or other signaling mechanisms. The signaling element may be attached to at least one of the first or second nucleic acid sequences. A signal from the signaling element may detectably change when the first and second nucleic acid sequences are not hybridized to one another.

The first nucleic acid sequence and the second nucleic acid sequence may each be 3-15 bases in length, for example. The first and second sequences may be chosen, for example, from among SEQ ID NO. 1 and 2, SEQ ID NO. 1 and 4, SEQ ID NO. 2 and 3, and SEQ ID NO. 3 and 4, or other pairs of similar length to allow double-stranded DNA stem formation. The first and second sequences of the stem may, for example, have melting temperatures at about 5° C.-15° C. or preferably about 10° C., above the reaction temperature. The non-nucleic acid linker may have a length, for example, that is comparable to the length of an oligonucleotide of 1-50 nucleic acid bases. For example, the linker may have a length that is about the same as or less than the length of a 50 base nucleotide sequence. In some aspects, the non-nucleic acid linker may be within the range of lengths comparable to the length of an oligonucleotide of 3-20 nucleic acid bases. The non-nucleic acid linker may, for example, be a nine-carbon linker tethered to or near the 3' end of the first nucleic acid sequence and to or near the 5' end of the second nucleic acid sequence. The linker may be attached to the end of the first nucleic acid sequence and to the 5' end of the second nucleic acid sequence, and if desired a signaling element may be positioned between the linker and either or both of the 3' and 5' ends of the first and second sequences. The term "near" as used in this paragraph may mean that some additional elements can be positioned between the linker and the 3' and 5' sequences. For example, in some aspects, there may be additional sequence or components between the linker and the sequences, such as a signaling element, which may be positioned between one or both ends of the linker and either or both of the 3' and 5' ends of the first and second sequences. Other components as desired, including additional nucleotides (e.g., 1-20) that do not hybridize, etc. also may be included.

The second nucleic acid sequence may be fused at or near its 3' end to the 5' end of an oligonucleotide sequence that may bind to a sequence of interest, including for example DNA derived from a pathogen, a human sequence or any other sequence of interest that is desired to be detected. The pathogen can be for example, a microbe. The pathogen can be, for example, a virus, a bacterium, a yeast, a protozoa, a fungus, and the like. Examples of viruses include, without being limited thereto, HIV, Hepatitis viruses (e.g., HBV, HCV), Dengue virus, Herpes viruses, West Nile virus, influenza and other flu-like viruses, pox viruses (e.g., chicken pox), and the like. Non-limiting examples of bacterial pathogens include *streptococcus, mycobacterium, staphylococcus, E. coli, Salmonella* and other enteric bacteria, syphilis, gonorrhea, tetanus, diphtheria, *Shigella*, and the like. Non-limiting examples of protozoa include protozoa that cause malaria, sleeping sickness, toxoplasmosis, Chagas, and the like. The oligonucleotide sequence that may bind to a sequence of interest may, for example, be chosen from one or more of SEQ ID NOs. 5-11.

The oligonucleotide sequence may, for example, bind to DNA in such a way as to facilitate the diagnosis, for example, of human genetic disorders. A non-exhaustive list of human genetic disorders for which screening primers are available and which may be used with some embodiments include the following disorders: Alpha-1-antitrypsin deficiency (AAT; emphysema and liver disease) Amyotrophic lateral sclerosis (ALS; Lou Gehrig's Disease; progressive motor function loss leading to paralysis and death) Alzheimer's disease (APOE; late-onset variety of senile dementia) Ataxia telangiectasia (AT; progressive brain disorder resulting in loss of muscle control and cancers) Gaucher disease (GD; enlarged liver and spleen, bone degeneration) Inherited breast and ovarian cancer (BRCA 1 and 2; early-onset tumors of breasts and ovaries) Hereditary nonpolyposis colon cancer (CA; early-onset tumors of colon and sometimes other organs) Central Core Disease (CCD; mild to severe muscle weakness) Charcot-Marie-Tooth (CMT; loss of feeling in ends of limbs) Congenital adrenal hyperplasia (CAH; hormone deficiency; ambiguous genitalia and male pseudohermaphroditism) Cystic fibrosis (CF; disease of lung and pancreas resulting in thick mucous accumulations and chronic infections) Duchenne muscular dystrophy/Becker muscular dystrophy (DMD; severe to mild muscle wasting, deterioration, weakness) Dystonia (DYT; muscle rigidity, repetitive twisting movements) Emanuel Syndrome (severe mental retardation, abnormal development of the head, heart and kidney problems) Fanconi anemia, group C (FA; anemia, leukemia, skeletal deformities) Factor V-Leiden (FVL; blood-clotting disorder) Fragile X syndrome (FRAX; leading cause of inherited mental retardation) Galactosemia (GALT; metabolic disorder affects ability to metabolize galactose) Hemophilia A and B (HEMA and HEMB; bleeding disorders) Hereditary Hemochromatosis (HFE; excess iron storage disorder) Huntington's disease (HD; usually midlife onset; progressive, lethal, degenerative neurological disease) Marfan Syndrome (FBN1; connective tissue disorder; tissues of ligaments, blood vessel walls, cartilage, heart valves and other structures abnormally weak) Mucopolysaccharidosis (MPS; deficiency of enzymes needed to break down long chain sugars called glycosaminoglycans; corneal clouding, joint stiffness, heart disease, mental retardation) Myotonic dystrophy (MD; progressive muscle weakness; most common form of adult muscular dystrophy) Neurofibromatosis type 1 (NF1; multiple benign nervous system tumors that can be disfiguring; cancers) Phenylketonuria (PKU; progressive mental retardation due to missing enzyme; correctable by diet) Polycystic Kidney Disease (PKD1, PKD2; cysts in the kidneys and other organs) Adult Polycystic Kidney Disease (APKD; kidney failure and liver disease) Prader Willi/Angelman syndromes (PW/A; decreased motor skills, cognitive impairment, early death) Sickle cell disease (SS; blood cell disorder; chronic pain and infections) Spinocerebellar ataxia, type 1 (SCA1; involuntary muscle movements, reflex disorders, explosive speech) Spinal muscular atrophy (SMA; severe, usually lethal progressive muscle-wasting disorder in children) Tay-Sachs Disease (TS; fatal neurological disease of early childhood; seizures, paralysis) Thalassemias (THAL; anemias—reduced red blood cell levels) Timothy Syndrome (CACNA1C; characterized by severe cardiac arrhythmia, webbing of the fingers and toes called syndactyl), autism). This list is not exhaustive. Other primers of interest in human disease diagnosis may also be used.

Without being limited thereto, the signaling element may include, for example, one or more of a FRET (fluorescence resonance energy transfer) signaling pair of molecules, a fluorophore coupled to a quencher, such as FAM coupled to a Dabcyl molecule, or any other suitable signaling element or signaling element pair, either coupled or acting singly.

The signaling element may be linked, for example, at or near either or both of the 5' end of the first sequence and at or near the 3' end of the second sequence, or it may be linked at or near either or both of the 5' end of the first sequence and at or near the 5' end of the second sequence, or it may be linked at or near either or both of the 3' end of the first sequence and at or near the 3' end of the second sequence, or it may be linked at or near either or both of the 3' end of the first sequence and at or near the 5' end of the second sequence.

Some embodiments relate to methods for detecting the amplification of a nucleic acid sequence. The methods may include, for example, contacting a sample that may include a nucleic acid with a set of primers under conditions necessary for amplification, wherein at least one of the primers has at its 5' end, a detection mechanism as described above or elsewhere herein.

Some embodiments relate to methods of quantifying the presence of an analyte or PCR product in a sample. The quantification may be accomplished, for example, by taking at least two measurements to determine a change in the signal over time and by correlating a change in signal with a corresponding duration of the amplification.

Some embodiments relate to kits comprising a detection mechanism as described above and elsewhere herein, along with of instructions for use as a detection mechanism.

Some embodiments involve the use of a primer with an incorporated auto-detection mechanism. For example, the auto-detection mechanism can include two nucleic acid sequences joined together by a non-nucleic acid linker. Mechanisms for detecting when two nucleic acid sequences are hybridized together are also included, e.g., using a fluorescence resonance energy transfer (FRET) pair. Some embodiments relate to methods of using detection primers to detect nucleic acid amplification products, including methods to detect real-time PCR products. In addition, some embodiments involve methods of using detection primers to quantitate an analyte. Some embodiments relate to methods of making the primers described herein.

In some embodiments, a detection primer can be designed for a highly conserved region across several species in which only a single base, for example, is not conserved. A detection primer capable of skipping the single variable base can be employed, thereby allowing the targeting of each species with a detection primer that has equal affinity for all targeted species. Examples of primers and primer technology that can be used with the detection mechanisms, primers, targets and methods disclosed herein can be found in U.S. application Ser. No. 12/830,242 filed on Jul. 2, 2010, entitled PRIMERS FOR NUCLEIC ACID EXTENSION OR AMPLIFICATION REACTIONS, which is incorporated herein by reference in its entirety.

In some embodiments, a highly polymorphic organism may have few regions of conservation, none of which are long enough for a primer with a stem-loop structure. However, by designing a detection primer which targets two or more of these short, conserved regions, the detection primer obtains sufficient affinity to be used in the reaction.

In some embodiments, several conserved regions of a target are of sufficient length to design a primer with an attached detection mechanism, but the content is poor due to excessive secondary structure, non-optimal GC content, overlap with other organisms, or other reasons known to one of ordinary skill in the art. By using a detection primer with a non-nucleic acid linker, short regions possessing preferred qualities for primer design may be targeted with sufficient affinity for amplification or extension to occur.

The detection primers described herein can be especially useful for any organism in which false negatives are possible due to high levels of polymorphism within species and/or low levels of sequence conservation across species. The methods and compositions described herein can be applied to many nucleic acid amplification and extension technologies.

The foregoing is a summary and thus contains, by necessity, simplifications, generalization, and omissions of detail; consequently, those skilled in the art will appreciate that the summary is illustrative only and is not intended to be in any way limiting. Other aspects, features, and advantages of the devices and/or processes and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings.

FIG. 1. Examples of Primers with Detection Mechanisms. (A) A detection primer is shown in which the detection mechanism consists of a FRET pair and two complementary nucleic acid sequences connected by an inert linker, where the FRET quencher is located between the inert linker and the first nucleic acid sequence. (B) A detection primer is shown in which the detection mechanism consists of a FRET pair and two complementary nucleic acid sequences connected by an inert linker, where the FRET quencher is located between the first nucleic acid sequence and the primer. (C) A detection primer is shown in which the detection mechanism consists of two complementary nucleic acid sequences connected by an inert linker with a fluorophore that possesses a different fluorescent output for single-stranded versus double-stranded conformations.

DETAILED DESCRIPTION

In the following detailed description, reference is made to the accompanying drawings, which form a part hereof. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

As used herein, the singular forms "a", "an", and "the" may refer to plural articles unless specifically stated otherwise. Thus, for example, references to a method of manufacturing, derivatizing, or treating "an analyte" may include a mixture of one or more analytes. Furthermore, the use of grammatical equivalents such as "nucleic acids", "polynucleotides", or "oligonucleotides" are not meant to imply differences among these terms unless specifically indicated.

To facilitate understanding of the disclosure that follows, a number of terms are defined below.

Definitions

The term "amplicon" refers to a nucleic acid product generated in an amplification reaction.

The term "amplification" refers to the process in which "replication" is repeated at least once, and preferably more than once in a cyclic process such that the number of copies of a nucleic acid sequence is increased in either a linear or logarithmic fashion.

The term "complementary strand" refers to a nucleic acid sequence strand which, when aligned with the nucleic acid sequence of one strand of the target nucleic acid, such that the 5' end of the sequence is paired with the 3' end of the other sequence in antiparallel association, forms a stable duplex. Complementarity need not be perfect. Stable duplexes can be formed with mismatched nucleotides.

The terms "detect," "detection" or "detecting the presence or absence of an analyte" refer to a process of providing qualitative or quantitative information about an analyte.

The term "normal hybridization conditions" refers to conditions under which complementary strands of DNA may specifically bind one another to form base-paired double helices. It excludes conditions for which temperature is too high to allow double helix formation, and it excludes conditions where the temperature is so low that a significant amount (e.g., about 5% or 10% to 100% or any amount or subrange therein) of single-stranded DNA molecules nonspecifically bind to one another, as may occur with samples left in tubes on ice.

The term "reaction temperature" refers to the temperature at which accurate base pairing or hybridization and/or extension occurs or may occur. For example, in some aspects the reaction temperature can be between about 25° C. and 95° C., preferably between about 45° C. and 60° C.

The terms "polynucleotide," "oligonucleotide" or "nucleic acid" refer to polydeoxyribonucleotides (DNA), polyribonucleotides (RNA), nucleic acid analogs and derivatives thereof. There is no intended distinction between the length of a "polynucleotide", "oligonucleotide" or "nucleic acid."

The term "primer" refers to an oligonucleotide that functions to initiate a nucleic acid replication, amplification or extension process.

The term "replication" refers to the process in which a complementary strand of a nucleic acid strand is synthesized by a polymerase enzyme. In a "primer directed" replication, this process generally requires a hydroxyl group (OH) at the 3' end of (deoxy)ribose moiety of the terminal nucleotide of a duplexed "primer" to initiate replication.

The term "single nucleotide polymorphism" (SNP) refers to a single-base variation in the genetic code.

The term "target" refers to an analyte to which a probe is designed to bind. In some embodiments, the target is the analyte which is being detected.

The term "variant" or "mutant" analyte refers to an analyte that is different than its wildtype counterpart.

The term "wildtype" as used herein refers to the typical form of an organism, strain, gene, or characteristic as it occurs in nature, as distinguished from mutant (e.g., forms that can result from selective breeding).

Analyte

In general, a primer is designed to specifically bind to a particular nucleic acid sequence. When referring to a primer, the phrase "specifically bind(s)" or "bind(s) specifically" refers to a primer that has intermediate or high binding affinity, exclusively or predominately, to a target molecule. The phrase "specifically bind(s) to" refers to a binding reaction which is predominant with the target in the presence of a heterogeneous population of other biologics. Thus, under designated assay conditions, the specified binding region binds preferentially to a particular target and does not bind in a significant amount to other components present in a test sample. Specific binding to a target under such conditions can involve a binding moiety that is selected for its specificity for a particular target. A variety of assay formats can be used to select binding regions that are specifically reactive with a particular analyte.

Sources of analytes can be isolated from organisms and pathogens such as viruses and bacteria or from an individual or individuals, including, but not limited to, skin, plasma, serum, spinal fluid, lymph fluid, synovial fluid, urine, tears, blood cells, organs, or tumors, and also samples of in vitro cell culture constituents, such as conditioned medium resulting from the growth of cells in cell culture medium, recombinant cells or cell components. Analytes can also be from environmental samples such as air or water samples, or may be from forensic samples from biological or non-biological sources, including clothing, tools, publications, letters, furniture, etc. Additionally, analytes can also come from synthetic sources. The analytes in the embodiments described herein can be provided in a sample that can be a crude sample, a partially purified or substantially purified sample, or a treated sample, where the sample can contain, for example, other natural components of biological samples, such as proteins, lipids, salts, nucleic acids, or carbohydrates.

A variety of modified and nonmodified nucleic acid bases can be used in the embodiments described herein. Examples include peptide nucleic acids, locked nucleic acids, 2'-halide ribose substitutions and numerous others known to one of ordinary skill in the art.

Each oligonucleotide primer in accordance with the embodiments described herein can vary from about 5 nucleotides in length to about 1,000 nucleotides in length.

In some embodiments, the primers are designed for maximum specificity. The melting temperature of the primer is preferably designed at between about 7° C. and about 10° C. over the reaction temperature. For assays that operate based on base-pairing between nucleotides, preferred primer lengths to achieve these melting temperatures preferably range between about 5 and about 25 bases, more preferably between about 10 and about 25 bases, and even more preferably between about 15 and about 25 bases.

In some embodiments involving primer design, large affinities may be desired for maximum sensitivity or to allow binding of variants. Melting temperatures for primers are preferably designed to be between about 10° C. to about 50° C. over the reaction temperature. For embodiments targeting nucleic acids, some primer lengths range preferably between about 20 and about 70 nucleotides, more preferably between about 25 and about 50 nucleotides, and most preferably between about 25 and about 40 nucleotides.

The melting temperature can be determined in an identical fashion to normal nearest neighbor thermodynamics calculations in primer design. In order to approximate melting temperature, nearest neighbor calculators such as Mfold can be employed. (M. Zuker, *Nucleic Acids Res* 31(13), 3406-15 (2003); D. H. Mathews et al., *J Mol Biol* 288, 911-40 (1999), which is incorporated herein by reference in its entirety). For example, both the primer and the target sequence can be entered into the Mfold software to calculate the melting temperature.

In preferred embodiments, the determination of the location of the primer binding sites can be made based on the degree of sequence conservation, uniqueness from other targets, optimal GC content, presence of little to no secondary structure, lack of self-complementarity and other factors known to one of ordinary skill in the art.

As with primer binding, melting temperatures of stem-loop structures can be predicted using software such as Mfold. Although the inert linker is not comprised of nucleic acid bases, this can be overcome by estimating the length of the linker in nucleic acid bases. For example, a 9 mer polyethylene glycol linker is the equivalent of approximately 9 nucleic acid base pairs in length. For calculations in programs like Mfold, a relatively inert sequence of nucleic acid bases can be used in the calculation (i.e., a string of 9 A's where the linker would be), or in some programs, the use of the symbol "N" is acceptable as well. "N" acts as an inert place holder, simulating the appropriate distance, but without participating in the reaction with other nucleic acid bases.

In some embodiments, the nucleic acid sequence in the detection mechanism portion of the primer is relatively GC-rich. High GC content increases the stability of the duplex.

In some embodiments the melting temperature of the nucleic acid sequence can be designed to be between about 0° C. and about 50° C. above the melting temperature. In a preferred embodiment, the melting temperature of the nucleic acid is designed to be between about 5° C. and about 20° C., and in more preferred embodiment, the melting temperature of the nucleic acid is designed to be between about 7° C. and about 12° C.

In some embodiments, preferred melting temperatures can be obtained by using partially complementary nucleic acid sequences. In some preferred embodiments, preferred melting temperatures are obtained by creating completely complementary sequences.

In some embodiments, the length of GC-rich complementary sequences in the detection region is, for example, between about 2 and about 10 base pairs to obtain optimal melting temperatures. In some preferred embodiments, the length is between about 3 and about 6 bases.

In the embodiments described herein, the linker type and length are important. Linkers comprised of nucleic acids are potentially reactive with other primers or nucleic acids in solution. Hence, it is important to select from the group of non-nucleic acid linkers known to one of ordinary skill in the art.

While there are many examples of such linkers, examples of those most commonly used at the present time in nucleic acid synthesis are carbon chain and polyethylene glycol linkers. In a preferred embodiment, inert linkers such as polyethylene glycol and/or carbon chains are used. However, other non-nucleic acid linker compositions may be used as well.

The linker length also can contribute to the melting temperature of the stem-loop structure. In preferred embodiments, the linker length is between about 3 and about 100 nucleic acid base equivalents. In more preferred embodiments, the linker length is between about 3 and about 18, or between about 3 and about 9 nucleic acid base equivalents.

Some embodiments provided herein relate to "kits" containing the elements necessary to carry out the methods described herein. Such a kit can include, for example, a detection mechanism and/or detection mechanism with a specific primer for detection of a target, for example. The kits can include a carrier being compartmentalized to receive in close confinement therein one or more containers, such as tubes or vials. One of the containers may contain at least one unlabeled or detectably labeled detection mechanism, primer or probe disclosed herein. The detection mechanisms, detection mechanisms with primer sequence, primer or primers can be present in lyophilized form or in an appropriate buffer as necessary. One or more containers may contain one or more enzymes or reagents to be utilized in PCR reactions. These enzymes may be present by themselves or in admixtures, in lyophilized form or in appropriate buffers.

Finally, the kit can include all of the additional elements necessary to carry out the methods disclosed herein, such as buffers, extraction reagents, enzymes, pipettes, plates, nucleic acids, nucleoside triphosphates, filter paper, gel materials, transfer materials, autoradiography supplies, and the like.

In some embodiments, the kits include additional reagents that are required for or convenient and/or desirable to include in the reaction mixture prepared during the methods disclosed herein, where such reagents include: one or more polymerases; an aqueous buffer medium (either prepared or present in its constituent components, where one or more of the components may be premixed or all of the components may be separate), and the like. The various reagent components of the kits may be present in separate containers, or may all be precombined into a reagent mixture for combination with template nucleic acid.

In addition to the above components, in some embodiments, the kits can also include instructions for practicing the methods disclosed herein. These instructions can be present in the kits in a variety of forms, one or more of which may be present in the kit. One form in which these instructions can be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address that may be used via the internet to access the information at a removed site. Any convenient means may be present in the kits.

The examples provided herein give those of ordinary skill in the art a disclosure and description of how to make and use some of the preferred embodiments, and are not intended to limit the scope of what the inventors regard as their invention. Modifications of the above-described modes for carrying out the some aspects of the technology that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

EXAMPLES

Example 1

Primers

Figure 1:
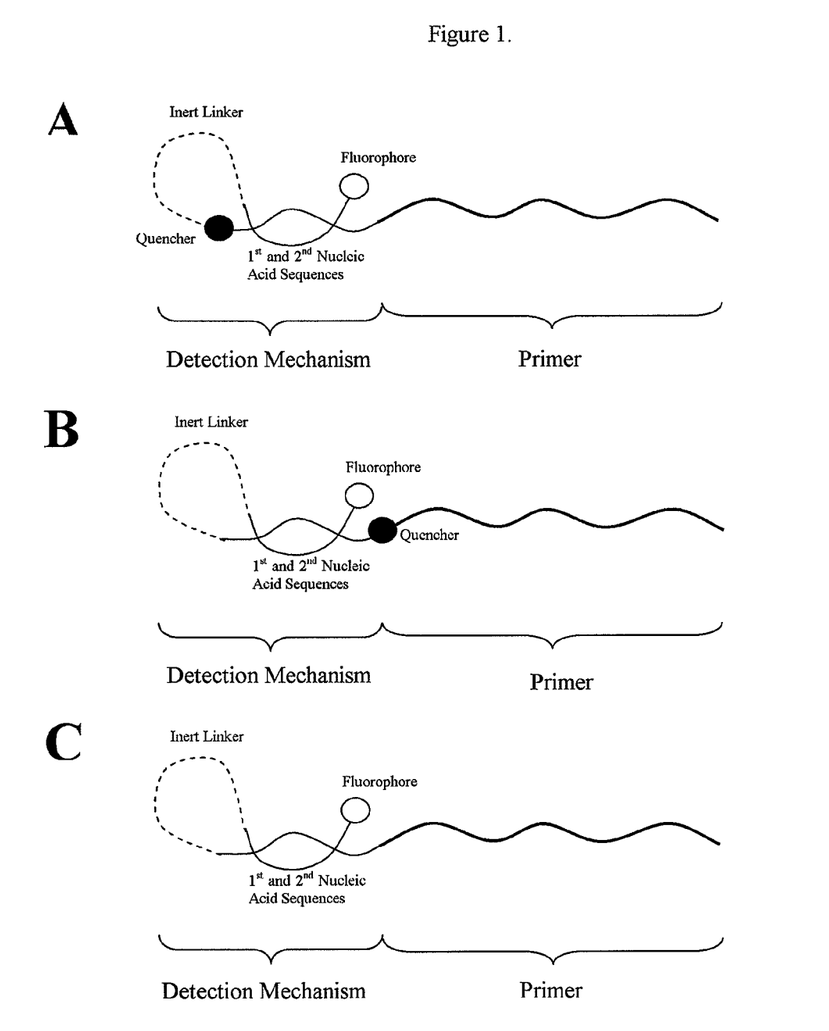

Examples of primers as described herein are shown in FIG. 1.

Example 2

Detection of Amplification Products

Figure 2:
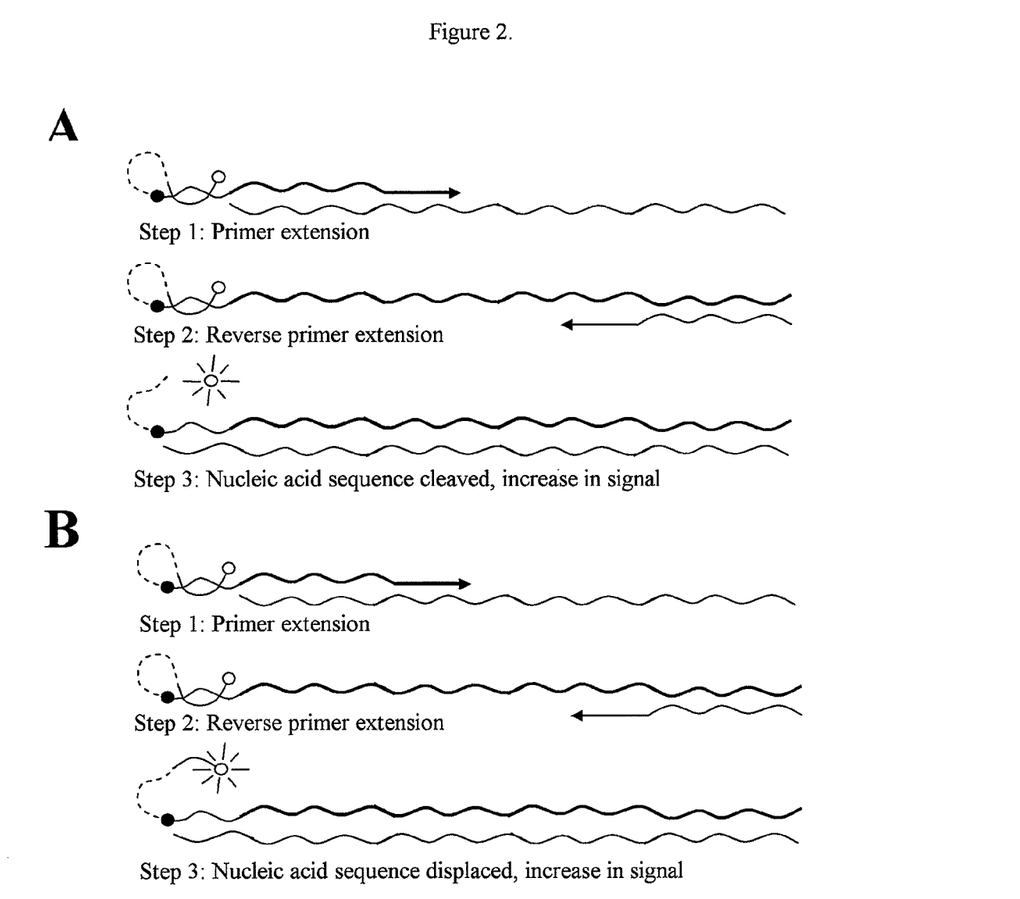
FIG. 2. Examples of the Detection of Amplification Products. (A) A method is shown in which a primer extends in step 1; a reverse primer extends in step 2; and the nucleic acid sequence is degraded, causing an increase in fluorescence in step 3. (B) A method is shown in which a primer extends in step 1; a reverse primer extends in step 2; and the nucleic acid sequence is displaced, causing an increase in fluorescence in step 3.

Examples of the mechanism of detection for an amplification product are shown in FIG. 2.

Example 3

Primer Sequences

Figure 3:
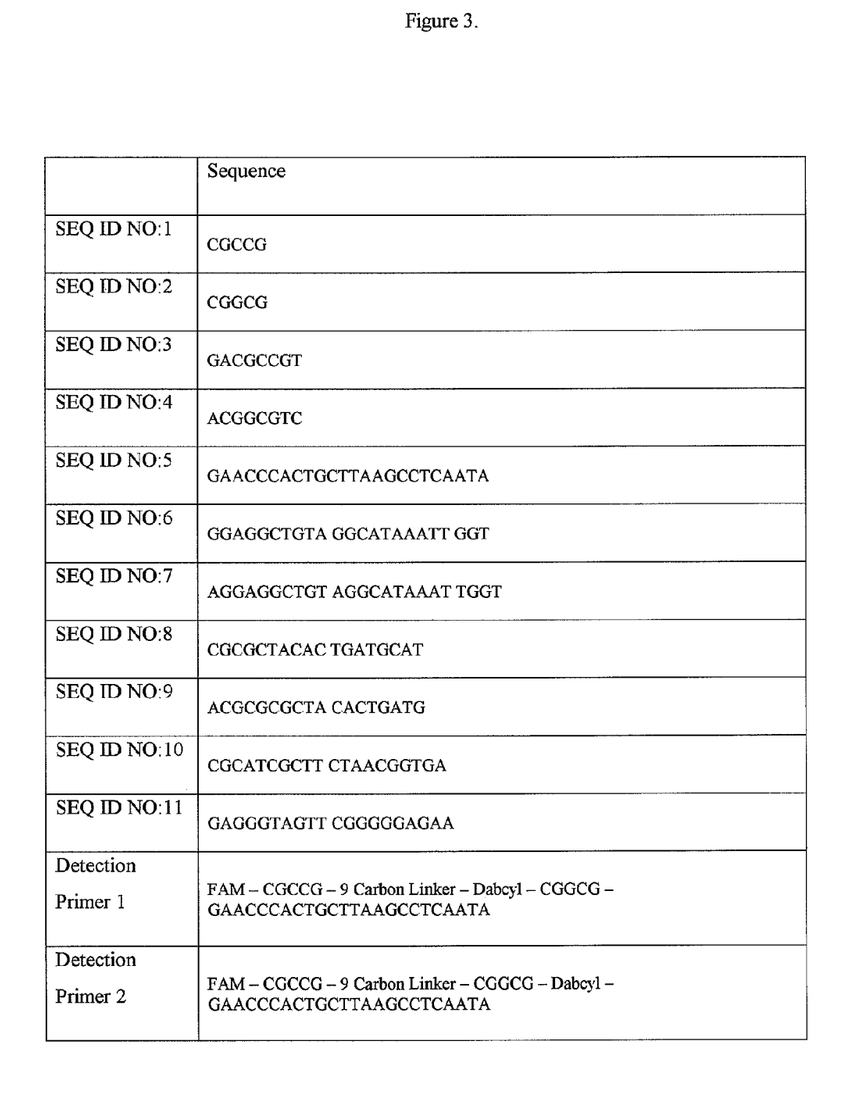
FIG. 3. Examples of Sequences for Primers with Detection Mechanisms. Exemplary sequences (i.e., Detection Primers 1 and 2) used in the detection of human immunodeficiency virus (HIV) are shown. Detection Primers 1 and 2 are identical, except for the position of the Dabcyl quencher.

Examples of primers created for the detection of HIV as described herein are shown in FIG. 3.

Example 4

Use of a Primer

Detection primer 1 (as shown in FIG. 3) is placed into a tube with 5 μL polymerase chain reaction master mix containing polymerase and reverse transcriptase with a reverse primer and 5 μL of purified HIV RNA. The reaction is carried out using a PCR cycling program consisting of a reverse transcription step at 55° C. for 10 minutes followed by a denaturing step at 95° C. for 20 seconds, followed by 45 cycles of 95° C. for 1 second and 55° C. for 20 seconds. Fluorescence is measured in the FAM channel during each 55° C. step. The presence of a sharp growth curve is indicative of the presence of HIV. The absence of a growth curve is indicative of the absence of HIV in the sample tested.

Example 5

Use of a Primer to Quantitate Analyte

Detection primer 2 (as shown in FIG. 3) is placed into a tube with 5 μL polymerase chain reaction master mix containing polymerase and reverse transcriptase with a reverse primer and 5 μL of purified HIV RNA. The reaction is carried out using a PCR cycling program consisting of a reverse transcription step at 55° C. for 10 minutes followed by a denaturing step at 95° C. for 20 seconds, followed by 45 cycles of 95° C. for 1 second and 55° C. for 20 seconds. Fluorescence is measured in the FAM channel during each 55° C. step.

A series of dilutions of HIV of known concentrations are simultaneously amplified. The cycle threshold values are plotted against the starting concentration of HIV. Using a fitted line, the concentration of the unknown HIV sample is interpolated.

What is claimed is:

1. A detection primer for initiating a nucleic acid amplification or extension reaction, comprising a primer coupled to a detection mechanism, wherein the detection mechanism comprises: a first nucleic acid sequence; a second nucleic acid sequence complementary to at least a portion of the first nucleic acid sequence, wherein the complementary sequence is between 3 and 10 base pairs in length, and wherein melting temperature of the complementary sequence is designed to be between 5° C. and 15° C. above reaction temperature; a non-nucleic acid, inert linker connecting the first and second nucleic acid sequences, wherein the linker length is between 3 and 9 nucleic acid base equivalents;

and a signaling element comprising one or more of a single signaling molecule, a pair of signaling molecules, a signaling molecule and a quenching molecule or other signaling mechanisms, wherein the signaling element is attached to at least one of the first or second nucleic acid sequences, wherein a signal from the signaling element detectably changes when the first and second nucleic acid sequences are not hybridized to one another.

2. The detection primer of claim 1, wherein the signaling element comprises a fluorophore wherein the fluorophore may emit a signal in the presence of double-stranded deoxyribonucleic acids (DNA) that is distinguishable from a signal that it may emit in the presence of single-stranded DNA.

3. The detection primer of claim 1, wherein the signaling element comprises a fluorescence resonance energy transfer (FRET) pair attached respectively to the first and second nucleic acid sequences, and wherein a detectable change in signal is a result of a change in the hybridization state of the first and second nucleic acid sequences to one another.

4. The detection primer of claim 1, wherein the detection primer comprises the following elements: a signaling element—CGCCG (SEQ ID NO:1)—a non nucleotide linker—CGGCG (SEQ ID NO:2)—a signaling element GAACCCACTGCTTAAGCCTCAATA (SEQ ID NO:5).

5. The detection primer of claim 1, wherein the detection primer comprises the following elements: FAM—CGCCG (SEQ IO NO:1)—9 Carbon Linker—CGGCG (SEQ ID NO:2)—Dabcyl—GAACCCACTGCTTAAGCCTCAATA (SEQ ID NO:5).

6. The detection primer of claim 1, wherein the detection primer comprises the following elements: CGCCG (SEQ ID NO:1)—a signaling element—a non-nucleotide linker—a signaling element—CGGCG (SEQ ID NO:2)—GAACCCACTGCTTAAGCCTCAATA (SEQ ID NO:5).

7. The detection primer of claim 1, wherein the detection primer comprises the following elements: CGCCG (SEQ ID NO:1)—FAM—9 Carbon Linker—Dabcyl—CGGCG (SEQ ID NO:2)—GAACCCACTGCTTAAGCCTCAATA (SEQ ID NO:5).

8. A kit comprising the detection primer of claim 5 and a set of instructions for use.

* * * * *